United States Patent [19]
Ting et al.

[11] Patent Number: 6,077,251
[45] Date of Patent: Jun. 20, 2000

[54] MEDICINAL AGENT ADMINISTRATION SYSTEM

[76] Inventors: Windsor Ting, 75 E. Hamilton Ave., Englewood, N.J. 07631; Joshua E. Tsitlik, 300 Winston Dr., Apt. 300, Cliffside Park, N.J. 07010

[21] Appl. No.: 08/961,124

[22] Filed: Oct. 30, 1997

[51] Int. Cl.$^7$ ...................................................... A61M 5/32
[52] U.S. Cl. ........................ 604/192; 604/187; 604/181
[58] Field of Search .................................. 604/43, 44, 143, 604/68, 191; 128/218

[56] References Cited

U.S. PATENT DOCUMENTS

| | | | |
|---|---|---|---|
| 4,007,739 | 2/1977 | Bron et al. | 128/218 |
| 4,790,817 | 12/1988 | Luther | 604/53 |
| 5,294,325 | 3/1994 | Liu | 204/418 |
| 5,304,128 | 4/1994 | Haber et al. | 604/68 |
| 5,480,389 | 1/1996 | McWha et al. | |
| 5,554,152 | 9/1996 | Aita et al. | 606/7 |
| 5,607,421 | 3/1997 | Jeevanandam et al. | |
| 5,769,824 | 6/1998 | Hjertman et al. | 604/143 |

OTHER PUBLICATIONS

P.K. Sen, et al "Further studies in multiple transmyocardial acupunture as a method of myocardial revascularization", Surgery, vol. 64, No. 5, (Nov. 1968).
Roque Pifarré, et al "Myocardial revascularization: Arterial and venous implants", J. of Thoracic and Cardiovascular Surgery, vol. 55, No. 3, Mar. 1968.
P. K. Sen, et al, "Transmyocardial acupuncture", J. of Thoracic and Vascular Surgery, vol. 50, No. 2, Aug. 1965.
Kuzela L., et al, "Experimental evaluation of direct transventricular revascularization" J. of Thoracic and Cardiovascular Surgery, vol. 57, No. 6, Jun. 1969.
Manuel White, et al, "Multiple Transmyocardial Puncture Revascularization in Refractory Ventricular Fibrillation due to Myocardial Ischemia", The Annals of Thoracic Surgery, vol. 6, No. 6, Dec. 1968.
Banning, G. Lary, "Effect of Endocardial Incisions on Myocardial Blood Flow", Archives of Surgery, vol. 87, Sep. 1963.
Banning, G. Lary, et al "Myocardial Revascularization Experiments Using the Epicardium", Arch. Surg., vol. 98, Jan. 1969.
Roque Pifarré, et al, "Myocardial revascularization by transmyocardial acupuncture", Transmyocardial Acupuncture, vol. 58, No. 3, Sep. 1969.

*Primary Examiner*—Thurman K. Page
*Assistant Examiner*—William E. Benston, Jr.
*Attorney, Agent, or Firm*—McAulay Nissen Goldberg Kiel & Hand, LLP

[57] ABSTRACT

An apparatus for intraorgan administration of medicinal agents, such as, cells, growth factors, drugs and other agents under direct visualization, for example using an endoscope, by an apparatus and method which create needle channels within the target organ and deposits by injection, the medicinal agent in high concentrations at designated sites of the target organ. The device consists of a chamber having at least one retractable hollow bore needle; a reservoir for containing an injectable medicinal agent which is in communication with the needle and control means for extending and retracting the needle from and into the chamber and forcing the medicinal agent from the reservoir into the needle and injecting it into a target organ, said control means being suitable for effecting control through an endoscopic tube. Also disclosed are injection needles having side openings therein for enhanced administration of the medicinal agent to the target organ.

14 Claims, 7 Drawing Sheets

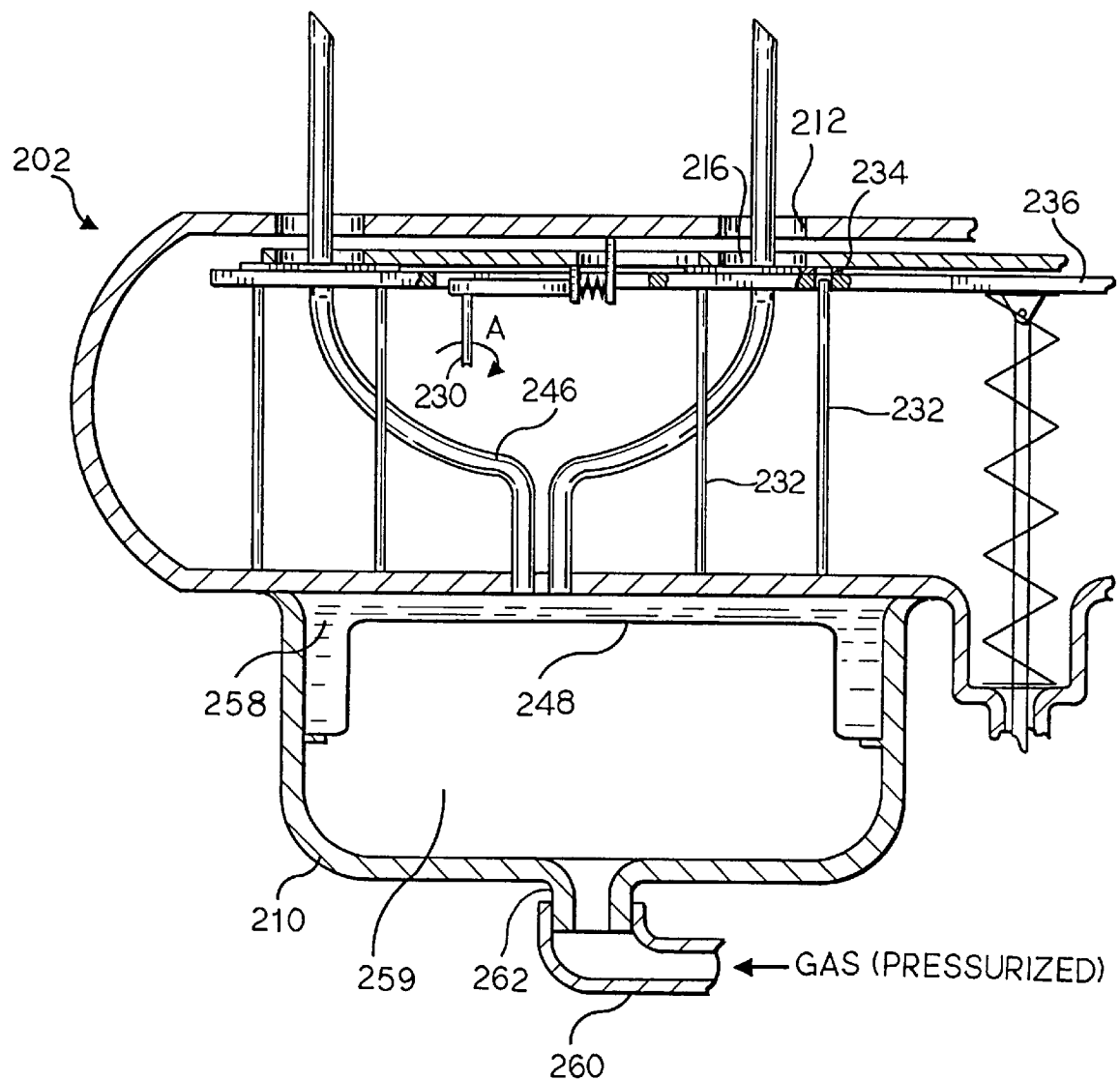
F I G. 4

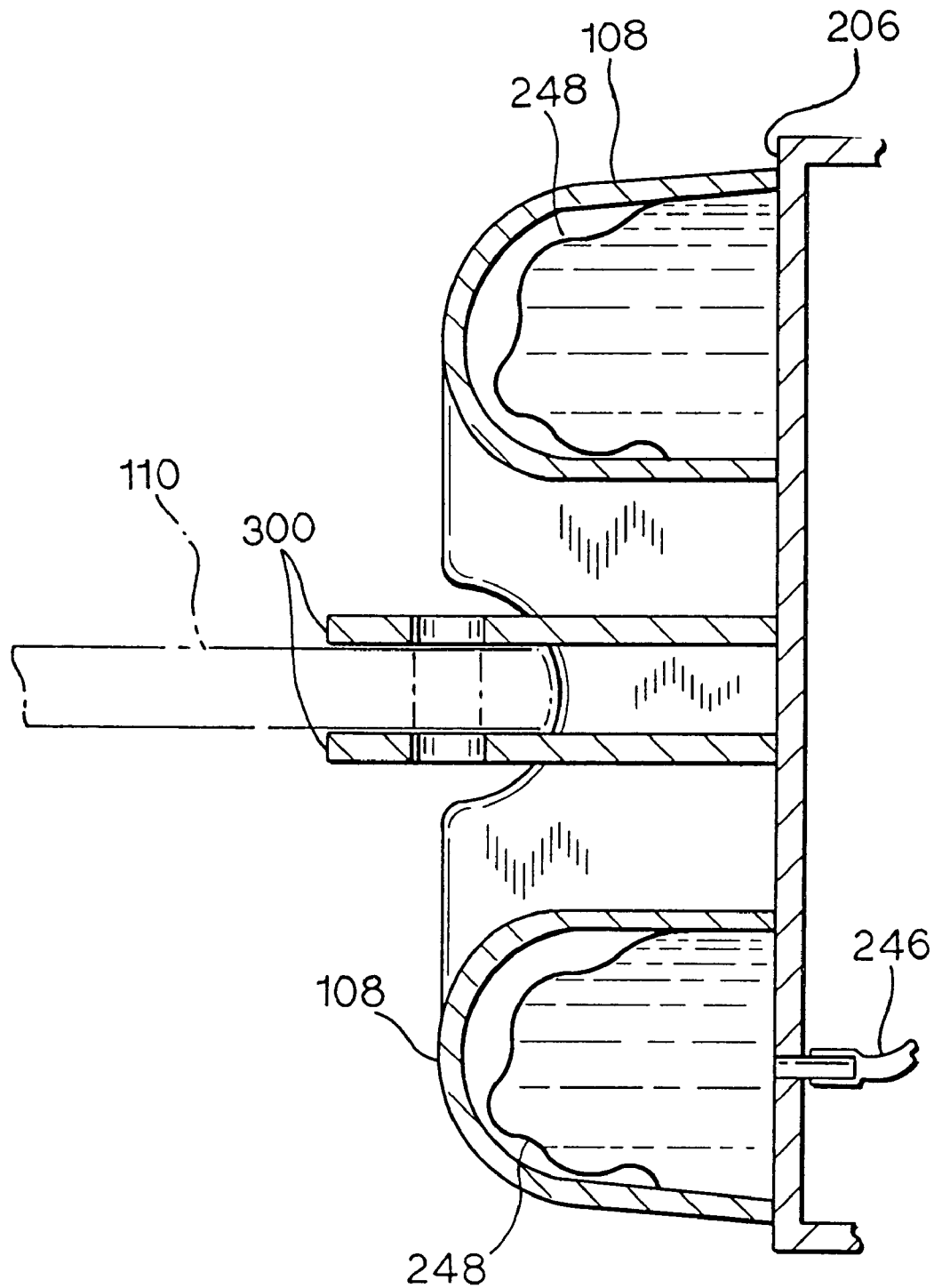
F I G. 5A

MEDICINAL AGENT ADMINISTRATION SYSTEM

FIELD OF THE INVENTION

This invention relates to a device and method for the administration of medicinal agents, such as, cells, growth factors, drugs and other agents into a designated site at a target organ under direct visualization.

BACKGROUND OF THE INVENTION

Current methods of drug and medicinal agent administration include oral, subcutaneous, intradermal, intramuscular, intravenous, intra arterial and transdermal approaches. They share the characteristic that they all utilize distribution via the circulatory system and systemic distribution. With these methods, therapeutic substances that are metabolized by circulatory factors will be rapidly degraded before reaching the target organ or achieving high concentration at the target site. Such methods are also ineffective for the delivery of cells to a specific target organ. For example, when using intravenous and intra arterial administration, the cells may become trapped in nonspecific capillary beds which can result in the failure of a substantial number of the cells from reaching the target site. If a high concentration of any therapeutic substance is required at a specific site, these current methods of drug delivery achieve this therapeutic level for the most part in a nonspecific fashion. As a result, concomitant high concentrations of the therapeutic substance are frequently observed at other organs and sites as well, resulting in undesirable side-effects.

Attempts to circumvent these obstacles by passing catheters in the arterial circulation to the target organ cannot be accomplished when the vessel is occluded from atherosclerosis or if the vessel is too small in caliber. Administration of therapeutic substances in either the arterial or the venous circulation also results in much of the therapeutic agent being lost to the systemic circulation from dilution and potentially rapid degradation. This is an important concern if the target site of therapeutic action is in the interstitial compartment and a high concentration of the therapeutic agent is required for effectiveness. Moreover, the entire organ cannot be visualized or examined directly during administration.

Recent research in growth factors, cellular transplantation, for example, the transplant of mature adult cells, xenograft cells, endo-secretory cells, genetically engineered cells, fetal cells and immune activated cells as well as drugs and immunotherapy, and other medicinal agents, suggest an important role for each of these entities in clinical medicine in the near future. The transition of this research into clinical applications will require an alternative drug delivery system other than the current methods. In particular, these new medicinal agents in some cases need to be administered directly to the tissue or organ which they will affect in order to maximize their medical efficacy and efficiency. The alternative delivery system will need to provide the ability to use direct target organ visualization and examination, allow for very precise delivery of the cells or therapeutic substances at the designated site(s), for example, a target organ in the body of a patient, with minimal systemic distribution and side-effects, and delivery of the cells and substances in high concentrations at the designated site(s), as well as ease of administration and safety for both the patient and the physician.

Growth factors and related substances are expensive, frequently available only in minute quantities and oftentimes are metabolized very rapidly in the systemic circulation. In order for these agents to be used as effective therapeutic agents, they must be delivered to a specific site, often within a very small area, at the target organ. The level of concentration of the growth factor and related substances must be high to be effective. Contact with the circulatory system must be minimal to avoid rapid degradation and dilution.

Another current approach using percutaneous single needle puncture guided by fluoroscopy, computer tomography scan or ultrasound is used primarily for diagnostic and drainage procedures. Many potential target organs are inaccessible by this approach. Localization is not precise enough and it does not provide for direct visualization and examination of the target organ. Furthermore, complications, such as bleeding, cannot be observed during the procedure.

Convergent with the above mentioned research is the rapid development of minimally invasive surgery. Prior to this, any direct visualization and examination of internal organs are performed through a formal operation. This is associated with pain and discomfort for the patient, potential complications, hospitalization and a variable period of convalescence. With minimally invasive surgery, the operative procedure is performed through three small "keyhole" incisions using special surgical instruments and endoscopic techniques and equipment. With the utilization of fiber optics and a monitor, the minimally invasive surgical approach can provide direct visualization and examination of organs in the abdomen, chest and elsewhere. Moreover, it is accomplished with minimal pain and discomfort to the patient. The patient is sometimes discharged as early as the day of the operation. The period of convalescence is short. At the present time, minimally invasive procedures are used for diagnosis and for treatment of diseases treated previously with conventional surgical procedures.

SUMMARY OF THE INVENTION

We have discovered a new apparatus and method for delivering medicinal agents directly to target organs and tissues and which is especially usefull with minimally invasive procedures. Specifically, the inventive device is composed of a unit for holding a liquid medicinal agent and injection means therefor. A first portion of the unit comprises an enclosed chamber having first and second opposing walls. Within the chamber is at least one hollow bore hypodermic needle having entrance and exit openings. The needle is capable of being positioned substantially perpendicular to the first wall and is movable between a first position wherein the needle is fully retracted within the chamber and a second position wherein the needle exit opening extends exterior of the chamber and a sufficient portion of the needle protrudes from the chamber to allow it to penetrate a target organ.

The first wall has openings which are opposite the exit openings of the needle when it is perpendicular to the first wall through which the needle can pass when moving between the first and second positions.

The chamber may also have access means for opening and closing the openings in the first wall so that, if desired, when the needle is retracted in the first position, the chamber is completely closed, and when it is desired to extend the needle for injection, the openings may be uncovered to allow the needle to pass there through.

A reservoir is attached to the second wall for holding a medicinal agent which is in injectable form. Conduits leading from the reservoir to the needle's entrance opening are provided for liquid communication between the reservoir and the needle. The reservoir also has means for moving liquid from the reservoir into and through the needles and out of the exit openings of the needles.

Flexible control means are connected to the unit for introducing it to the interior of a patient's body through an endoscopic tube, and for positioning it adjacent a target organ or tissue be injected. This same control means may have means for controlling the access means to open and close the openings in the first wall, to move the needle between the first and second positions and for forcing liquid from the reservoir through the conduits into the needle and out of the needle exit into the target organ or tissue. The present invention is suitable for use in more conventions surgical procedures wherein access to the interior of a patient's body is through another type of opening in a patient's body, such as an incision or a bodily aperture, e.g., anus, vagina, mouth, nostril, etc.

Accordingly, several objects and advantages of the present invention are:

(a) to provide a delivery system for medicinal agents, including cells, growth factors, drugs and other therapeutic agents;

(b) to provide a delivery system that can administer the medicinal agents to a specific site in a target organ or tissue;

(c) to provide a delivery system that can administer medicinal agents to a target organ or tissue under direct visualization in a minimally invasive approach;

(d) to provide a delivery system that can concurrently offer direct examination of the diseased target organ;

(e) to provide a delivery system that can access organs directly in the abdomen, chest and elsewhere in the body;

(f) to provide a delivery system that can administer medicinal agents in high concentration to a specific site at the target organ or tissue;

(g) to provide a delivery system design that is flexible and may be adaptable to different clinical applications;

(h) to provide a delivery system that may find clinical applications in transplantation, immune disorders, and diseases of the cardiovascular, endocrine, hepatobiliary, gastrointestinal and other organ systems; and (i) to provide a delivery system that can efficiently distribute a medicinal agent onto an extended area of an organ or tissue.

BRIEF DESCRIPTION OF THE DRAWINGS

FIG. 4 is a view similar to FIG. 2 showing a position of a device in accordance with the present invention with needles in an extended position;

FIG. 5A is a view along the lines 5A-5A' of FIG. 5;

DETAILED DESCRIPTION OF THE PREFERRED EMBODIMENT

The inventive apparatus may be configured in a range of sizes, diameters, and lengths depending on the clinical application and the target organ. It may be made of disposable or reusable materials. Generally, the apparatus is introduced via an access port using endoscopic devices and techniques into the abdomen, chest, or elsewhere in the body. One or more additional access ports provide access for fiberoptic cables and manipulating instruments for visualization, examination, retraction of adjacent organs, concurrent procedures, and guiding the intra organ administration system. Such endoscopic devices and techniques are known in the art.

Figure 1:
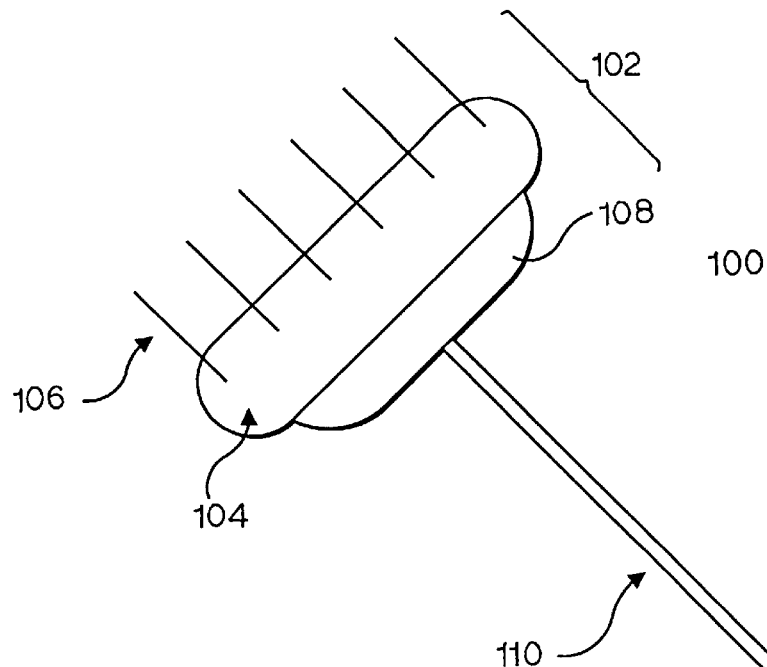
FIG. 1 is a perspective overall view of the apparatus of the invention.

FIG. 1 depicts an embodiment of the apparatus. Additional components may be added, depending on the clinical requirements. As shown, the inventive device 100 comprises unit 102 composed of chamber 104, containing needles 106 shown in extended form. Reservoir 108 is attached to the back of chamber 104. Control means 110, usually in the form of a flexible hollow tube is attached to unit 102 for controlling various functions from a position exterior of the body. This control means 110 is intended to allow the unit 102 to be introduced to the body interior via an endoscopic tube as well as to extend through an endoscopic tube and allow manipulation and positioning of unit 102 and needles 106 by the clinician, as well as to allow transference of the medicinal agent to the needles.

The unit 102 is available in different sizes and shapes as well as other specifications depending on the clinical requirements. The unit is retractable or is connected to the control means by a pivotal mechanism described hereinafter. After insertion into the abdomen, chest or elsewhere in the body, the unit is engaged. Similarly, the needles on the unit are either protected by a sleeve, retractable through a spring-like mechanism or connected to the unit by pivotal mechanisms. These design considerations are made to minimize the diameter of the apparatus for passage through the access port and to avoid injury to adjacent organs and tissues. The needles may be configured in different arrays in the chamber. The number of needles, the length of the needles and the diameter of the needles are available in a variety of options. Needles are available with a single opening or with fenestrations at one level or multiple levels. This permits a variety of ways by which the cells or therapeutic substances are distributed within the target organ. The opening and fenestrations are closed during insertion into target organ and are opened after insertion. Puncture of the target organ by the needles may be achieved by either direct pressure or a spring-like mechanism in the cartridge.

Figure 2:
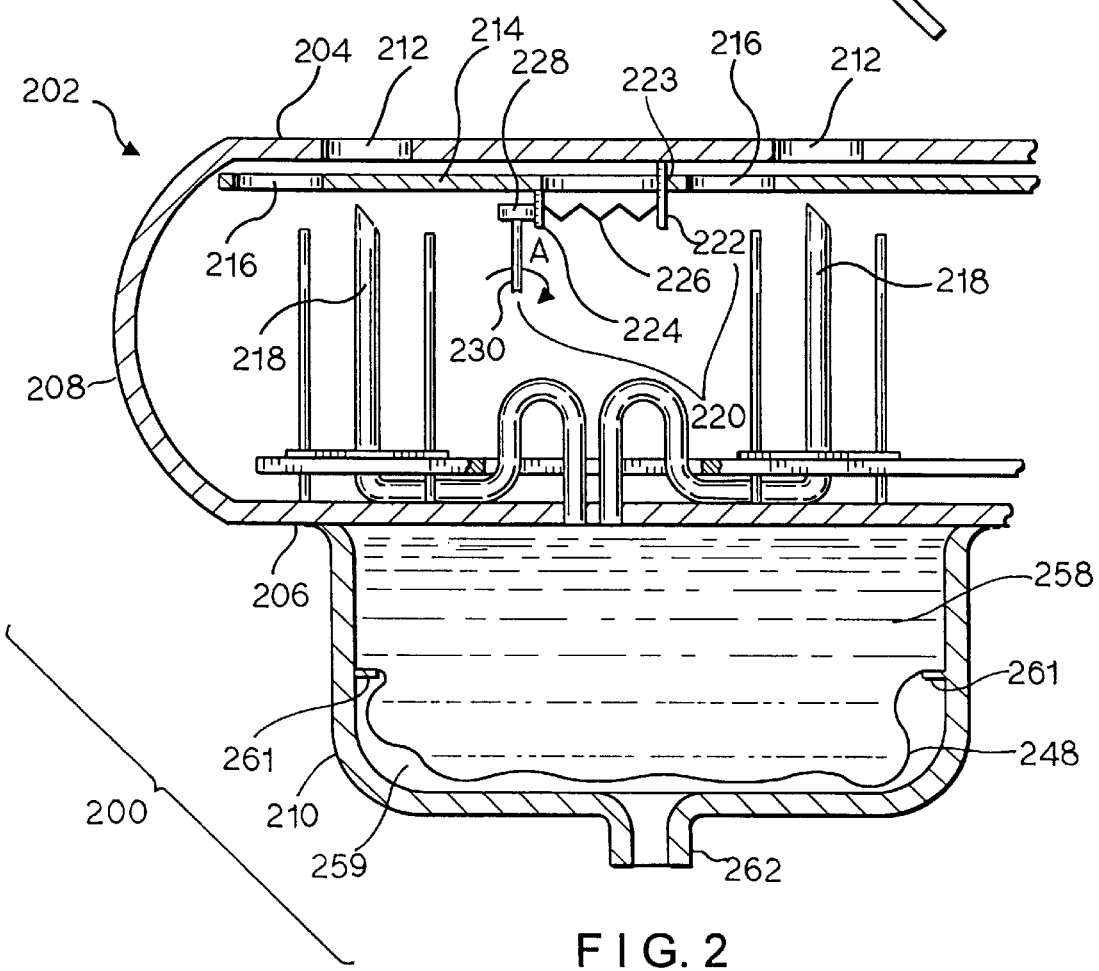
FIG. 2 is a partial cross-section of the a device in accordance with the present invention.

Referring to FIG. 2, unit 200 is composed of chamber 202 having two opposing walls, namely, front wall 204 and rear wall 206, connected by side wall 208. Reservoir 210 is attached to the rear wall 206.

Front wall 204 has openings 212 therein. Inner plate 214 is mounted inside chamber 208 adjacent front wall 204 and in slidable relationship therewith. Inner plate 214 is slidable between a first closed position and a second open position with respect to front wall 204. Inner plate 214 has openings 216 therein, which are positioned so that they may be aligned with openings 212 when inner plate 214 is in the second open position. In the first closed position, openings 216 are out of alignment with openings 212. Thus, in the first position, the chamber is closed because openings 216 are completely out of alignment with openings 212. As used herein, "completely out of alignment" means that no part of openings 216 are adjacent or in alignment with openings 212. When inner plate 214 is moved to the second or open position, openings 216 are in complete alignment with openings 212, allowing needles 214 to pass through the openings and project exterior of the chamber as will be described hereinafter. In the first closed position, the contents of the chamber and the reservoir are protected. Inner plate 214 is slidably secured to front wall 204 by a mounting bracket (not shown).

Movement of inner plate 214 between the first and second positions is effected by a positioning mechanism generally depicted as 220. This is composed of a shoulder 222 secured to front wall 204 and which protrudes through inner plate 214 through an elongated slot 223 such that inner plate 214 may slide back and forth relative to shoulder 222.

Figure 3:
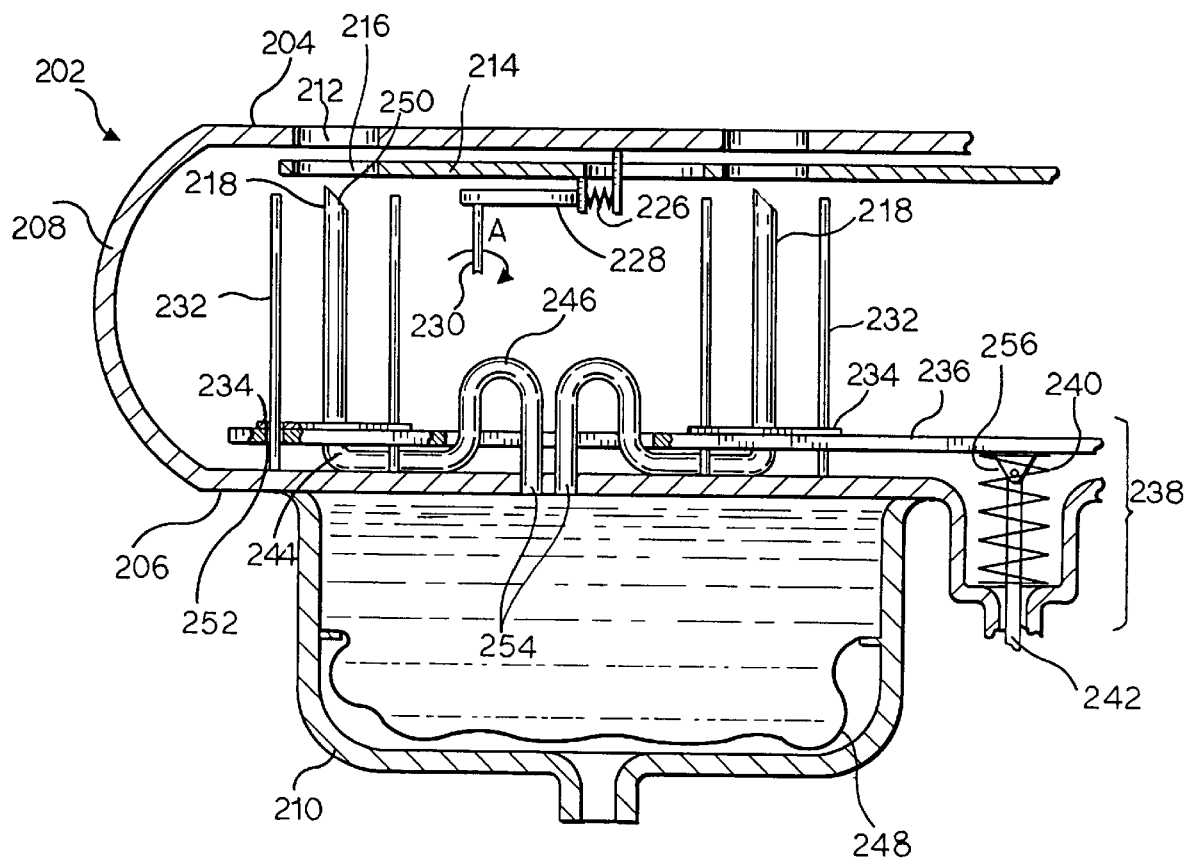
FIG. 3 is a view similar to FIG. 2 showing an open position of a device in accordance with the present invention.

Shoulder 224 is fixedly mounted on inner plate 214 and shoulders 222 and 224 are connected by spring 226. When spring 226 is in the uncompressed state, inner plate 214 is in the first closed position such that holes 212 an 216 are completely nonaligned. Shoulder 224 is in contact with cam member 228 which is rotatably mounted against shoulder 224 and may be turned by shaft 230. Shaft 230 may be formed in part or completely of flexible materials and extends exterior of chamber 202 through control means 110. However this is not shown in order to simplify the drawing. Rotation of shaft 230 in the direction of arrow A rotates cam 228 and moves shoulder 224 towards shoulder 222, thus compressing spring 226, moving inner plate 214 into the second open position and openings 216 into full alignment with openings 212 as depicted in FIG. 3.

Flexible membrane 248 is of an appropriate plastic or film material which is both liquid, e.g., water, and gas impermeable and is secured at each end on side flanges 261 attached to the inner side walls of reservoir 210 so as to divide reservoir 210 into inner and outer sub-chambers, 258 and 259, respectively. Inner chamber is for containment of the medicinal agent and outer chamber 259 has an inlet 262 therein for introduction of a pressurized gas as described hereinafter.

As used herein, the term "proximal" means a position on an element closer to the clinician and the term "distal" means a position away from the clinician and closer to the target. As also shown in FIG. 3, needles 218 are positioned in alignment with openings 212 in front wall 204. Needles 218 are hollow tubular hypodermic needles having a pointed distal opening 250, and a proximal opening 244. Needle 218 has a flange 234 adjacent its proximal end 244 which, in turn, is mounted onto bar 236. Flange 234 and bar 236 have aligned apertures 252 therein. Upright pins 232 are secured to rear wall 206 and flanges 234 and bar 236 are slidably positioned onto pins 232 through apertures 252 so that bar 236, flanges 234 and needles 218, may be moved back and forth along pins 232 which maintain the alignment of needles 218.

The open proximal end 244 of needle 218 extends through flange 234 and bar 236 (FIG. 4) and is attached to flexible conduit or tube 246, the other end of which communicates with the interior of inner sub-chamber 258.

As shown in detail in FIGS. 3 and 4, needles 218 are moveable between two positions, a first in which the needles are inside chamber 202 and retracted from the outside and a second position wherein the needles protrude through apertures 216 and 212 exterior of chamber 208 for injection. The needles are moved between these two positions by needle control means indicated generally at 238. Needle control means is mounted through rear wall 206 and comprises a lock mechanism 256 attached to a control rod 242 which extends outside of rear wall 206 and through an appropriate endoscopic tube exterior of the body to be controlled by the clinician. Positioned between bar 236 and rear wall 206 is spring 240, which, when the needles 218 are fully retracted within the chamber, is in a compressed state and is held there by lock mechanism 256. When lock mechanism 256 is released by manipulation of rod 242, spring 240 is released and pushes bar 236 and, in turn, needles 218, towards front wall 204 and through apertures 212 into the organ or tissue to be injected. This position of needles 218 in the extended position is shown more specifically in FIG. 4. As can be seen, spring 240 is in an extended state, bar 236 has been pushed fully forward against inner plate 214, and the needles 218 project through apertures 216 and 212 and are presumably penetrating or may be pushed into the organ or tissue to be injected.

After penetration of needles 218 into the organ or tissue, gas pressure applied through conduit 260 attached to reservoir inlet 262, pushing membrane 248 towards rear wall 206 and forcing the medicinal agent in inner sub-chamber 258 into and through conduits 246 and into and out of needles 218 and into the organ or tissue. The amount of medicinal agent injected may be controlled by controlling the gas pressure applied to membrane 248 as well as the amount of medicinal agent initially placed in inner sub-chamber 258.

After the desired amount has been injected, bar 236 may be pulled back towards rear wall 206 by manipulation of rod 242, and the mechanism is recocked so that the needles are again fully retracted to a position within the chamber. Shaft 230 may then be rotated so as to slide inner plate 214 into a position whereby apertures 212 and 216 are completely out of alignment, thus once again, closing off the chamber. The unit may then be removed from the interior of the body through the appropriate endoscopic tube.

It will be appreciated that inner sub-chamber 258 will be charged with the medicinal agent through a port (not shown) prior to insertion of the device into the body and an amount of the medicinal agent will be introduced into conduits 246 and needles 218 to purge any air or other gas therein and prepare them for injection into the organ or tissue.

Figure 5:
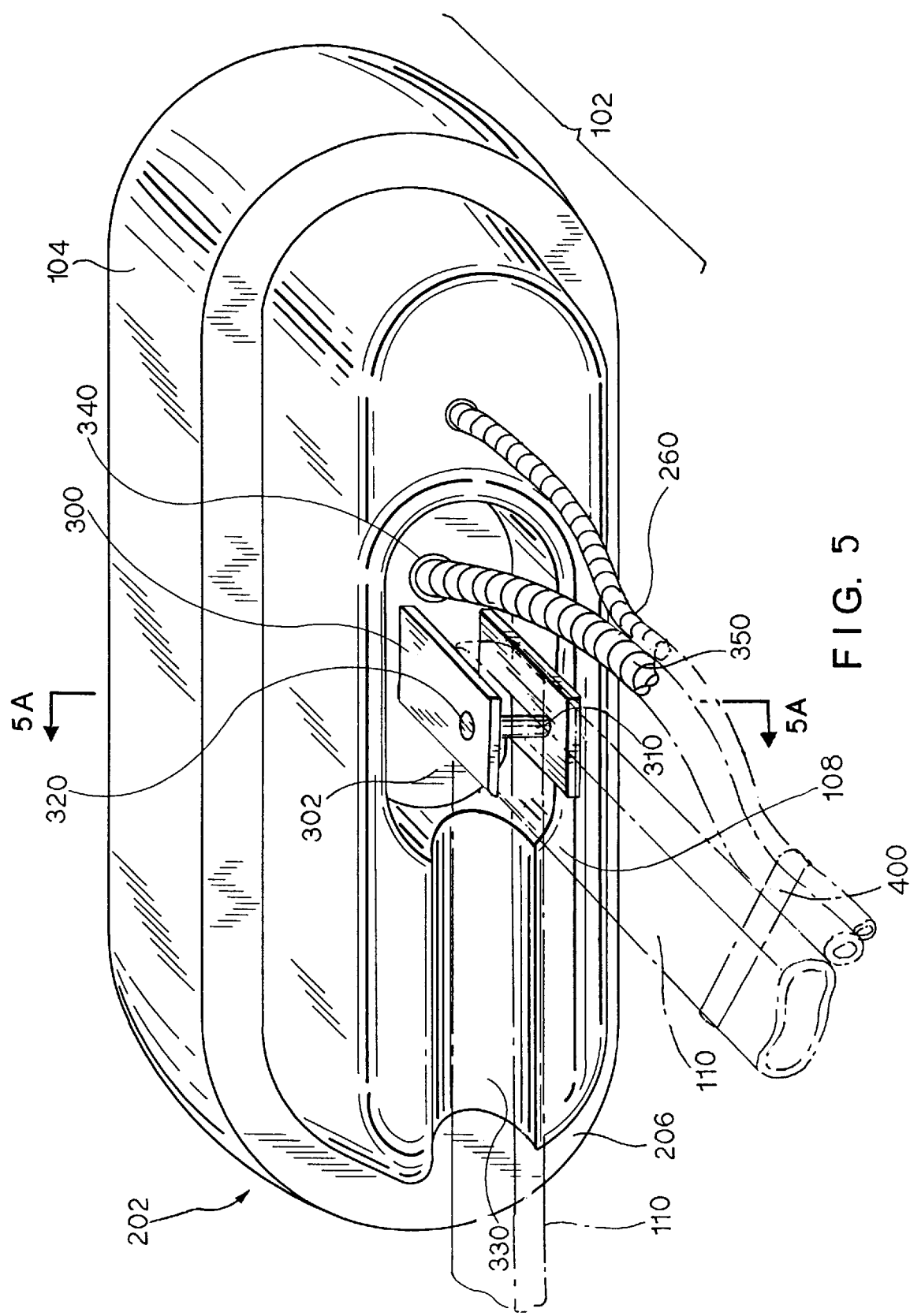
FIG. 5 is a view in perspective of the bottom of a device in accordance with the present invention.

FIG. 5 shows a bottom perspective view of unit 102 and in particular, shows the positioning of a reservoir 108 on the bottom on chamber 104. Reservoir 108 has an elliptical donut shape with an aperture 302 in the middle to allow access to rear plate 206. This allows control means 110 to be attached to the bottom of rear plate 206. As shown, control means 110 is essentially a flexible tube which is sized appropriately to allow containment or attachment of various rods, as needed, to, for example, move inner plate 214 between its two positions and manipulate rod 242 of injection control means 238 so as to extend and retract the needles 218 from the chamber. In the embodiment shown in FIG. 5, conduit 350 is a flexible tube which contains rods for these manipulations and is attached to control means 110 by tie 400. Additionally shown is a gas conduit 260 which is attached to the bottom of reservoir 108 and which is further attached to conduit 350 and control means 110 by tie 400. Conduit 350 and gas conduit 260 may actually be inside conduit 110 for at least a portion of their length. Gas conduit 260 is also a flexible tube which extends through the endoscopic tube used in connection with the invention.

As will be appreciated, it is necessary for unit 102 along with its pertinent conduits to fit through an endoscopic tube into the body cavity for placement at the tissue for organ. For this purpose, unit 102 is rotatably attached to an insertion rod or handle, which is not shown in this Figure. In particular, the rod is attached to a pin 310 which is secured between two posts 300 which are attached to rear wall 206. The pin goes through the rod or handle and device 102 may rotate about pin 310 relative to the handle. A depression 330 in reservoir 108 is provided so that for insertion purposes, the device 102 may be aligned longitudinally with the rod in order to present a sufficiently small cross-section for insertion through the endoscopic tube. Once the device has been inserted through the tube and positioned at the organ or tissue to be injected, it may then be rotated so as to be positioned so that the front wall 204 can be pressed against the organ or tissue to be injected.

It is also possible for the handle or rod to be the control means 110 and have conduit 350 and gas conduit 260 attached to it.

FIG. 5A shows a cross-section of reservoir 108 along the lines 5A-5A' of FIG. 5. Control means 110 is shown in phantom to illustrate its rotatable positioning between plates 300.

Figure 6:
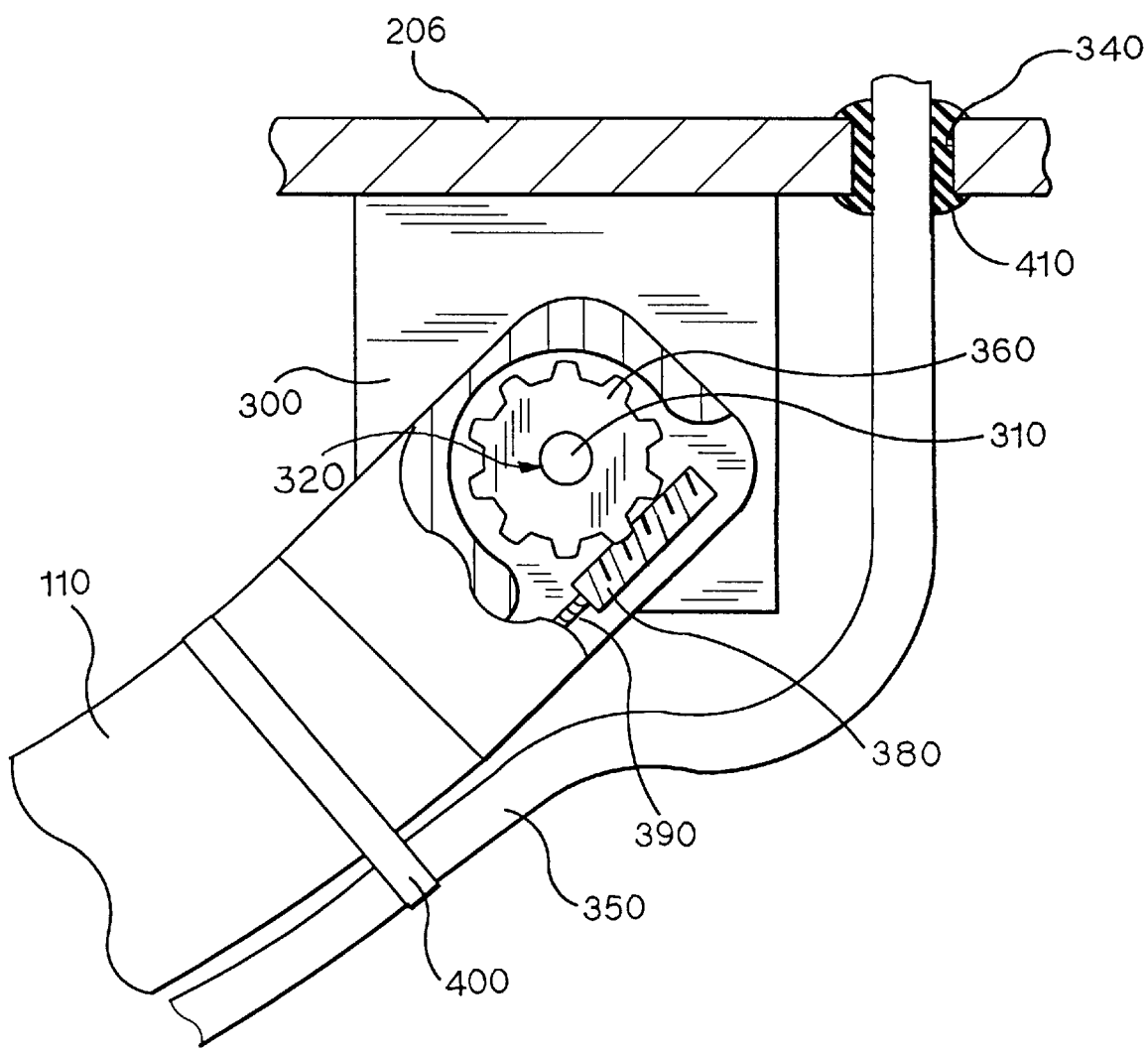
FIG. 6 is a cross-sectional partly open view of the control means of a device in accordance with the invention.

FIG. 6 shows in detail, a mechanism for controlling the rotation of unit 102 relative to control means 110. Thus, control means 110 can rotate about pin 310 which is mounted in hole 320 of post 300. Gear 360 is rigidly mounted onto pin 310. A worm 380 is mounted in the handle so it can be rotated by a cable 390 which is within control means 110 and extends out through the endoscopic tube. As a result of twisting cable 390, worm 380 rotates gear 360 and therefore the unit about the pin 310 so as to place the front plate 204 (not shown in FIG. 6) in the desired position adjacent or against the organ or tissue to be injected. As noted, upon initial insertion, unit 102 will be parallel to control means 110 for ease of insertion through the endoscopic tube. However, after insertion is achieved, rotation of cable 390 allows the clinician to rotate the unit 102 about pin 310 so as to achieve the desired position.

Also shown in FIG. 6 is a separate conduit 350 which is secured to the control means 110 by tie 400. Conduit 350 is routed into chamber via an aperture 340 which has a gas and liquid tight seal 410.

As shown in the embodiments of FIGS. 2, 3 and 4, the needles 218 are conventional hypodermic needles in that the distal opening is beveled or pointed to allow penetration of tissue. Such a needle has only one exit opening at its proximate end for transference of the medicinal agent there through into the organ or tissue.

We have found that in order to increase the efficiency of the distribution of the medicinal agent in the organ or tissue, it is desirable that the medicinal agent be dispensed from the needle along its length as opposed to only at the proximate end. For this purpose, we have discovered a new hypodermic needle as depicted in FIGS. 7 and 8.

Figure 8:
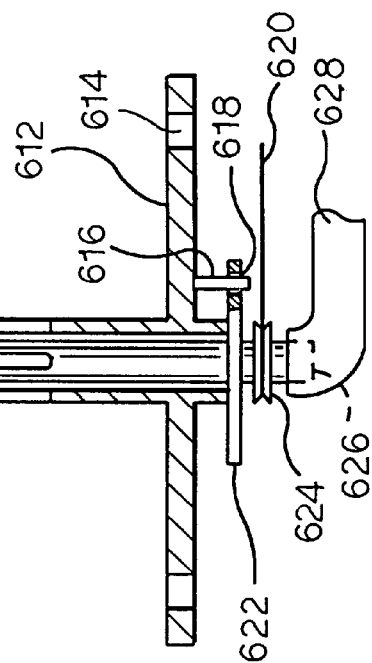
FIG. 8 is a cross-sectional view in detail of a mounted hypodermic needle in accordance with the present invention.
Figure 7:
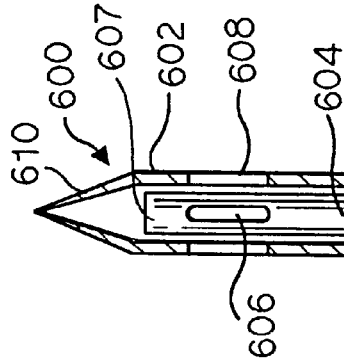
FIG. 7 is a perspective view of an inventive hypodermic needle in accordance with the present invention.

FIGS. 7 and 8 depict the hypodermic needle in accordance with the present invention which achieves this greater efficacy of delivery of the medicinal agent. Needle 600 is composed of an outer tube 602, and an inner tube 604. Inner tube 604 is slidably insertable into outer tube 602 and is rotatable relative to outer tube 602. Outer tube 602 contains fenestrations 606 which, as shown, are elongated and staggered along the length of outer tube 602. Similarly, inner tube 604 contains fenestrations 608 having the same configuration as fenestrations 606. When inner tube 604 is fully inserted into outer tube 602, upon rotation of the tubes relative to one another, fenestrations 606 and 608 come into full alignment. In the same manner, by rotation of inner tube 604 relative to outer tube 602, the fenestrations may be adjusted to be completely out of alignment in which case the tube is closed so that no liquid medicinal agent can pass therethrough. In this connection, it is noted that although the inner and outer tubes are slidable and rotatable in relation to each other, the fit between them is such that neither liquid nor gas will be admitted to or can travel along their interface.

A mechanism by which the relative rotation of tubes 602 and 604 may be controlled is also depicted in FIGS. 7 and 8. As shown, outer tube 602 has at the proximal end, flange 612 having holes 614 therein for placement of the alignment pins, e.g., pins 232 as depicted in FIG. 3. Proximal end 626 of the inner tube 604 extends beyond flange 612 so as to protrude therefrom and provide a tip for attachment of conduit 628 which is the same conduit 246 depicted in FIG. 3. A disk 622 having a cut-out portion or notch 618 is attached to inner tube 604 near its proximal end 626. Situated between disk 622 and proximal end 626 and mounted on inner tube 604 is a pully member 624. String 620 is wrapped around pully 624 and is controlled by a mechanism (not shown) for movement of the pully. Pulling of the string in a given direction results in rotation of inner tube 604 so that the fenestrations 606 and 608 may be moved into and out of alignment as required for injection. The control mechanism for string 620 may be manipulated, for example, through conduit 350. Pin 616 is attached to flange 612 and cooperates with notch 618 to limit the relative rotation of the inner and outer tubes such that, in essence, the tubes can only be moved between their extreme positions, the first being a position in which the fenestrations in each tube are completely out of alignment in which case medicinal agent cannot be injected through the needle and a position where the fenestrations in each tube are completely in alignment and medicinal agent can be injected through the needle.

In FIG. 7, the distal end 610 of needle 600 is closed so that medicinal agent cannot be dispensed from the end but rather only through fenestrations 606 and 608 and only when the fenestrations are in alignment with one another. Additionally, inner tube 604 is lugged or otherwise sealed at the distal end 607 at a level 611 which is even with the distal end of the most distal fenestration of the needle. This allows the purging of any air from the inner tube, when the inner tube is filled with liquid medicinal agent prior to use. As can be seen, when the fenestrations in the inner and outer tubes are in alignment with one another, liquid medicinal agent will be dispensed from needle 600 over a substantial portion of its length which allows delivery of the medicinal agent to a greater interior area of the organ or tissue into which the needle has been inserted.

The embodiment of FIG. 8 provides an easy method of ensuring that no air pockets remain in the needle once the needle is filled with the medicinal agent. The needle in FIG. 8 is identical to the needle of FIG. 7, with the following exceptions: the distal end of the inner tube 604 comes to a point and fully fills the outer tube 602; the outer tube 602 contains a terminal fenestration 700 which is aligned radially with at least some of the outer tube's other fenestrations 608 and vents the most distal portion of the hollow interior of outer tube 602; and the inner tube 604 contains a terminal fenestration 710 which is completely out of alignment radially with any of the inner tube's other fenestrations 606 and vents the most distal portion of the hollow interior of inner tube 604. As used herein, "completely out of alignment radially" means that no part of inner tube terminal fenestration 710 is in alignment with another fenestration of inner tube 604, such that when inner tube terminal fenestration 710 is in alignment with outer tube terminal fenestration 700, none of the inner tube fenestrations 606 are even partially in alignment with outer tube fenestrations 608. The inner tube terminal fenestration must also be placed so as to still allow the complete closure of the needle, i.e. allow a rotation position of the inner tube and outer tube relative to each other such that no fenestrations are aligned and the medicinal agent cannot be injected through the needle.

The needle of FIG. 8 is filled by rotating the inner and outer tubes relative to each other until the terminal fenestrations are aligned and applying gas pressure to the reservoir inlet 262 sufficient to fill conduit 246 and the needle, thereby purging the conduit and needle of all trapped gasses. The needle is then closed by rotating the inner and outer tubes relative to one another. In this position, no liquid can escape from the needle. At the time it is desired to inject the liquid medicinal agent, the inner tube is rotated such that the fenestrations 606 and 608 are in alignment. However, fenestrations 700 and 710 are out of alignment. Pressure may then be applied to the reservoir and the medicinal agent will exit the needle along its length through fenestrations 608.

We claim:

1. An apparatus for the injection of medicinal agents directly into an organ of the body of a patient comprising:
   A. a unit for holding a liquid medicinal agent and injection means therefore, said unit comprising:
      1) a chamber having first and second opposing walls;
      2) at least one hollow bore hypodermic needle having entrance and exit openings mounted in the chamber, the needle being movable between a first retracted position wherein the needle is fully within the chamber and a second extended position wherein the needle exit opening extends exterior of the chamber;
      3) the first wall having an opening therein to allow the needle to pass therethrough when moving between the first and second positions;
      4) access means for opening and closing the opening in the first wall:
      5) a reservoir attached to the second wall for containing a medicinal agent in liquid form;
      6) conduits providing liquid communication between the reservoir and the entrance opening of the needle;
      7) liquid transfer means for moving liquid from the reservoir, through the needles and out of the exit openings of the needles; and
   B. control means connected to said unit for introducing it to the interior of a patient's body through an opening therein, positioning the device adjacent an organ or tissue to be injected, controlling the access means to open and close the opening in the first wall, moving the needle between the first and second positions and forcing liquid from the reservoir through the conduits into the needle and out of the needle exit.

2. The apparatus of claim 1 where the access means comprises:
   a) a plate adjacent the first wall having openings therein corresponding to the openings in the first wall and being slidable between a first closed position in which openings in the first wall and plate are completely out of alignment and a second open position in which the openings in the first wall and the plate are in alignment to allow the needles to pass there through, and
   b) positioning means for moving the plate between the open and closed positions.

3. The apparatus of claim 2 wherein the positioning means comprises a first shoulder secured to the first wall and protruding through an aperture in the plate, a second shoulder secured to the plate, the first and second shoulders being connected to each other by a compressible spring, a cam member rotatably mounted and in contact with one shoulder for compressing the spring, means for rotating the cam to move the first and second shoulders to positions away from or towards each other corresponding to the first closed and second open positions of the plate.

4. The apparatus of claim 1 wherein the liquid transfer means comprises a flexible, liquid and gas impermeable membrane dividing the reservoir into first and second chambers, the first chamber having conduit means connecting it with the entrance opening of the needle, and the second chamber being connectable to gas pressure means for pressurizing the second chamber and forcing liquid out of the first chamber and into the needles.

5. The apparatus of claim 1 wherein the control means for moving the needle between the first retracted and second extended positions comprises a needle connection means attached to the needle, a spring positioned between the needle connection means and the second wall and movable between compressed and uncompressed positions corresponding to the first retracted and second extended positions, a control rod connected to the spring for moving the spring between the compressed and uncompressed positions, and lock means for locking the spring in the compressed and uncompressed positions.

6. The apparatus of claim 1 which further comprises an insertion rod, a swivel connector securing the insertion rod to the second wall, the insertion rod and unit and reservoir being rotatable between a first insertion position where the insertion rod, unit and reservoir are aligned parallel to each other so as to present a minimal cross section for insertion into an opening in a patients body, and a second, injection position wherein the insertion rod is substantially perpendicular to the unit and reservoir so that the first wall can be placed against a tissue or organ to be injected.

7. The apparatus of claim 1 having a plurality of needles.

8. The apparatus of claim 1 wherein the needle comprises;
   a) an outer hollow bore needle having a tubular side wall and having a closed end adapted for insertion into tissue, the side wall having a plurality of openings therein;
   b) an inner hollow bore needle having a tubular side wall positioned within the outer needle, the side wall having a plurality of openings therein corresponding to and alignable with the openings in the side wall of the outer needle;
the outer and inner needles being rotatable relative to one another between a first closed position wherein the openings in one needle are not aligned with any openings in the other needle and a second open position wherein the corresponding openings in each needle are aligned with one another.

9. The apparatus of claim 8 wherein the hypodermic needle further comprises rotation means for rotating the outer and inner needle between the first closed position and the second open position.

10. The apparatus of claim 9 wherein the rotation means comprises a pulley attached to the inner tube, and belt means attached to the pulley for turning the pulley.

11. The apparatus of claim 1 wherein the needle comprises:
   a) an outer hollow bore needle having a tubular side wall and pointed terminal end with an apex adapted for insertion into tissue, a side wall having a plurality of side fenestrations distributed throughout and the pointed end having a single terminal opening in the side wall which vents the apex of the pointed end;

b) an inner hollow bore needle having a tubular side wall positioned within the outer needle, the side wall having a plurality of side fenestrations therein corresponding to and alignable with the fenestrations in the side wall of the outer needle, the inner hollow bore needle having a terminal opening for venting the inner hollow bore needle and corresponding to and alignable with the terminal opening of the outer needle;

the outer and inner needles being rotatable relative to one another between a first closed position wherein the terminal opening and fenestrations in one needle are not aligned with any terminal opening or fenestrations in the other needle, a first open position wherein the side corresponding fenestrations in each needle are aligned with one another and a second open position wherein the terminal opening in one needle is aligned with the terminal opening in the other needle, but none of the corresponding side fenestrations in each needle are aligned with one another.

12. The apparatus of claim 11 which further comprises rotation means for rotating the outer and inner needle between the first open, first closed and the second open positions.

13. The apparatus of claim 12 wherein the rotation means comprises a pulley attached to the inner tube, and belt means attached to the pulley for turning the pulley.

14. In a surgical procedure wherein an opening is used to provide access to the interior of a patient, a method for injection of a medicinal agent directly into tissue or an organ of the patient using the apparatus of claim 6, comprising introducing the medicinal agent in to the first chamber of the reservoir, placing the unit, reservoir and insertion rod into the first insertion position, inserting the unit and reservoir through the opening into the patient, placing the unit and reservoir into the second injection position and in contact with the tissue or organ to be injected, opening the opening in the first wall, moving the needle into the second extended position so as to pierce the tissue or organ, and activating the liquid transfer means to transfer the medicinal agent from the reservoir, through the needle and into the tissue or organ.

* * * * *